United States Patent [19]
Berger

[11] 3,996,305
[45] Dec. 7, 1976

[54] FRACTIONATION OF AROMATIC STREAMS

[75] Inventor: Charles V. Berger, Western Springs, Ill.

[73] Assignee: Universal Oil Products Company, Des Plaines, Ill.

[22] Filed: Mar. 27, 1975

[21] Appl. No.: 562,511

[52] U.S. Cl. .................. 260/672 T; 260/674 R; 260/674 SE
[51] Int. Cl.$^2$ ............................................ C07C 3/62
[58] Field of Search ...... 260/672 T, 674 SE, 674 R

[56] References Cited
UNITED STATES PATENTS

| | | | |
|---|---|---|---|
| 3,527,825 | 9/1970 | Pollitzer ........................ | 260/672 T |
| 3,551,510 | 12/1970 | Pollitzer et al. ................ | 260/672 T |
| 3,701,813 | 10/1972 | Stenmark ...................... | 260/672 T |
| 3,729,521 | 4/1973 | Gatberlet et al. .............. | 260/672 T |

Primary Examiner—C. Davis
Attorney, Agent, or Firm—James R. Hoatson, Jr.; Thomas K. McBride; William H. Page, II

[57] ABSTRACT

A novel fractionation scheme applicable to a transalkylation process in which an admixture of toluene and $C_9$ alkylbenzene is converted to principally benzene and $C_8$ alkylbenzene is disclosed. Transalkylation zone effluent containing $C_6$–$C_{10}$ alkylbenzene or a $C_6$–$C_{10}$ alkylbenzene admixture of transalkylation zone effluent and extract from an aromatics separation zone is passed into a fractionation zone wherein an admixture of benzene and toluene is withdrawn as a lower boiling fraction, $C_8$ alkylbenzene is withdrawn as a central boiling fraction, and $C_9$ and $C_{10}$ alkylbenzne are withdrawn in admixture as a higher boiling fraction. The lower and higher boiling fractions are introduced into a fractionator at a higher and a lower locus, respectively. From the fractionator, an overhead fraction containing benzene and a bottoms fraction containing $C_{10}$ alkylbenzene are withdrawn as product streams, and one or more sidecut fractions including toluene and $C_9$ alkylbenzene are withdrawn and recycled to the transalkylation zone.

2 Claims, 1 Drawing Figure

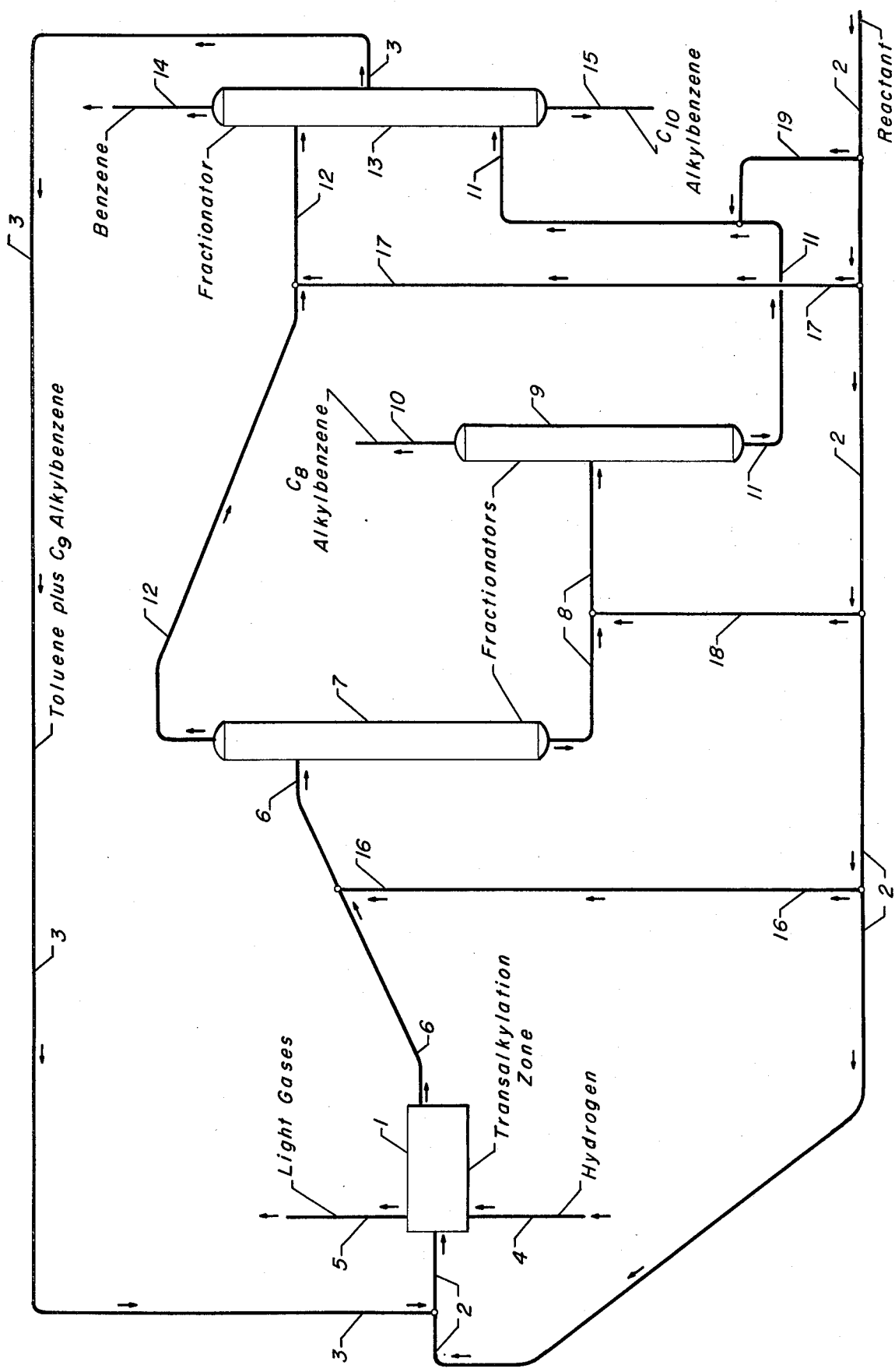

FRACTIONATION OF AROMATIC STREAMS

BACKGROUND OF THE INVENTION

The present invention relates to a process in which an admixture of toluene and $C_9$ alkylbenzene is transalkylated to form benzene and $C_8$ alkylbenzene. It specifically relates to fractionation of the reaction zone effluent of a process in which an admixture of toluene and $C_9$ alkylbenzene is transalkylated to benzene and $C_8$ alkylbenzene.

At the present time, about 90 percent of the benzene produced in the U.S. is derived from petroleum sources and the balance is derived from natural gas and coal. This represents a sharp change from as recently as 1957 when the steel and coal industries produced more benzene than did the petrochemical industry. This is in large part due to the high growth rate of benzene demand experienced during the past decade, averaging 12 percent per year during that time, but also reflects a stagnation of benzene production by tar distillers and coke oven operators. About 85 percent of benzene consumption in the U.S. now goes to production of ethylbenzene, phenol, and cyclohexane, while a relatively small amount goes to aniline, maleic anhydride, chlorobenzene and other uses. Ethylbenzene, which consumes 48 percent of U.S. benzene production, is an intermediate chemical in the production of styrene, and is prepared principally from benzene (90 percent) by alkylation with ethylene, with fractionation of mixed aromatics derived from petroleum supplying the remainder. Styrene is used principally for the production of styrene-butadiene rubber and styrene resins such as polystyrene, both the straight and rubber-modified polystyrenes finding application in consumer products such as packaging, toys, luggage, housewares, etc. Twenty percent of benzene production is used to prepare phenol, which is produced by various methods, principally by way of cumene as an intermediate, and is itself an intermediate chemical in the production of phenolic resins, which are used in molding applications, plywood bonding, laminating resins, friction materials, thermal insulation, etc. And 17 percent of benzene production goes to produce cyclohexane, an intermediate in the manufacture of nylon. Because of benzene's use in the production of consumer goods, it is expected that demand will continue strong, but perhaps not at the annual growth rate of 12 percent experienced during the past decade due to benzene's present unit cost more or less quadruple that of the previous decade.

Like benzene, demand for xylene has been strong principally due to increasing demand for paraxylene. Over the past decade, while yearly production of mixed xylene has increased 9 percent, that of orthoxylene has increased 13 percent and that of paraxylene has increased 24 percent. Xylenes are produced almost solely from petroleum, with less than 2 percent production from coaltar and coke oven light tars. Xylene isomers together with ethylbenzene as produced from petroleum are normally found as follows as related to the total $C_8$ aromatic: ethylbenzene 15–25 percent, orthoxylene 15–25 percent, metaxylene 35–45 percent, and paraxylene 12–22 percent. As stated hereinabove, ethylbenzene is used in the production of styrene; orthoxylene is a feedstock in the production of phthalic anhydride while paraxylene is used for polyester manufacture.

Benzene, ethylbenzene, and the xylene isomers are principally prepared and separated together with toluene from petroleum by a series of processing units as follows: (1) In a crude unit, crude petroleum is fractionated into several boiling range cuts, one of which is a naphtha cut which boils in a range of about 100° to 350° F. (2) After epentanizing or deisohexanizing of the naphtha, it is passed to a desulfurization and reforming unit, where sulfur is removed to less than one part per million and the aromatic precursors in the naphtha are upgraded to their respective aromatics. (3) Reforming unit effluent, normally containing about 30 to 60 percent aromatics, is passed into an aromatics extraction unit, wherein normally either a glycol or sulfolane is utilized as a solvent to extract aromatic components from non-aromatic ones. Extract containing about 99.9 percent aromatics is clay treated to reduce olefin content and is separated in a fractionation zone to prepare the various aromatic components in purified streams as desired. Several important variables affect the quantity of individual aromatic products obtained by the hereinabove processing scheme, the most important of them being the quality of the crude and the market for products. Crudes vary significantly in quality in regard to aromatic and aromatic precursor content, and in regard to the ratio of aromatics and aromatic precursors by carbon number. While there is significant variation, benzene, toluene, and xylene (including ethylbenzene) are typically produced in the following ratio:

```
          benzene = 1
          toluene = 2.5 to 3.0
xylene and ethylbenzene = 2.0 to 2.5
```

Although it appears that the production rates of toluene and xylene may be greater than that of benzene, toluene, and xylene U.S. production in 1973 were 1453, 936, and 818 million gallons, respectively. Consumption is far greater of benzene than toluene, or xylene, and accordingly, production of toluene and xylene is restricted, normally by one of two means. Firstly, a naphtha cut with an end point of about 230°–300° F. may be processed, thereby substantially reducing the toluene and xylene precursors in the reforming unit feedstock; and secondly, a dealkylation unit may be utilized to convert toluene to benzene. A further explanation of higher benzene production than toluene or xylene is related to the aromatics production from coke-oven light oils, coaltar, and pyrolysis processes, which is similar from these sources in distribution of benzene, toluene, and xylene produced. While there may be substantial variation from one producer to another, benzene, toluene and xylene comprise about 80, 15 and 5 percent, respectively, of the BTX aromatics produced in these processes.

Toluene, unlike benzene, orthoxylene, and paraxylene, does not have strong demand as an intermediate chemical in the manufacture of consumer products. End uses such as polyurethane production, aviation gasoline, or solvents require only about 35 percent of U.S. production; the remainder of U.S. toluene production is dealkylated to benzene. In the present description, U.S. production of aromatics stated hereinabove is the production and separation into relatively purified streams of said aromatics, but in fact, total production is substantially greater. For example, only about 20 percent of total toluene produced is actually separated into a purified stream, the remainder being used as a high octane gasoline blending component. As a blending component, toluene has a premium value with a research octane number of 105.8. With the present emphasis on lead-free gasoline, high octane blending components such as toluene are becoming relatively more valuable than previously, but toluene dealkylation has increased and now accounts for about 32 percent of benzene production as compared to about 22 percent in 1965. Accordingly, it is observed that toluene dealkylation is becoming an increasingly attractive route to benzene production.

Both thermal and catalytic toluene dealkylation processes are available to produce benzene. Both catalytic and thermal dealkylation are practiced in the presence of hydrogen at high reaction temperatures of about 1200°–1300° F. to achieve over 95 percent dealkylation to benzene. Both processes may accept feedstock including alkylaromatics higher than toluene, and these are also normally converted to benzene although mild conversion of $C_9$ and heavier aromatics to xylene is known in the art. Feedstocks including paraffins, naphthenes, and aromatics are also provided to both dealkylation processes to result in benzene and light paraffin products, i.e., methane and ethane. Because of high hydrogen consumption and low benzene volume yields, dealkylation to benzene of alkylaromatics heavier than toluene is not as advantageous as toluene dealkylation.

A relatively new process development is a catalytic transalkylation process in which toluene is transalkylated to benzene and xylene in the presence of hydrogen. The process is advantageous as compared with dealkylation processes in the respect that hydrogen consumption is substantially reduced and reaction temperatures are less severe. In a transalkylation process in which toluene is a feedstock, the principal reaction taking place is as follows:

Molar yields of benzene and xylene are essentially achieved in the process, and while the theoretical volume yield of benzene from toluene is about 84 percent by dealkylation, the combined theoretical volume yields of benzene and xylene is about 100 percent from transalkylation of toluene. Of the $C_8$ aromatic product, only 1 to 2 percent is ethylbenzene, with the xylene isomers comprising the remainder in the following proportions: para 23–25 percent, meta 50–55 percent and ortho 23–25 percent.

In addition to benzene and $C_8$ aromatic products, about 2 to 4 percent of the reactant is converted to light hydrocarbons, such as methane and ethane, and heavy aromatics containing 10 or more carbon atoms. An alkylaromatic product containing 9 carbon atoms is produced in the reaction, but following separation of the reaction zone effluent, it may be recycled to extinction in the reaction zone. Although the primary reactant introduced into the process is toluene, $C_9$ aromatic may also be used and upgraded principally to xylene and a $C_{10}$ aromatic. For example, trimethylbenzene is principally converted to xylene and tetramethylbenzene.

The process of the present invention is applicable to a transalkylation process in which toluene reactant alone or $C_9$ alkylbenzene alone is contemplated, but is particularly directed toward a process in which an admixture of toluene and $C_9$ alkylbenzene is introduced into the process and is transalkylated in a reaction zone wherein complete conversion of the reactants is not achieved, thus requiring separation and recycling to the reaction zone of unreacted reactants. Application of the present invention is unique to a process in which toluene and $C_9$ alkylbenzene in admixture are transalkylated to form benzene and $C_8$ alkylbenzene products.

SUMMARY OF THE INVENTION

An object of the present invention is to provide an improved process in which toluene alone, $C_9$ alkylbenzene alone, or an admixture thereof is transalkylated to provide benzene and xylene products.

A specific object of the invention is to reduce energy consumption in a transalkylation process to convert toluene and $C_9$ alkylbenzenes to benzene and xylene.

A more specific object of this invention is to provide an improved fractionation scheme in which admixed, unreacted toluene and $C_9$ alkylbenzene are separated from benzene and xylene products of a transalkylation reaction zone effluent.

In an embodiment, the present invention relates to a transalkylation process for producing principally benzene and $C_8$ alkylbenzene products comprising the steps of: (a) transalkylating an admixture of toluene and $C_9$ alkylbenzenes in a transalkylation zone at transalkylation conditions to result in transalkylation zone effluent including benzene, toluene, $C_8$ alkylbenzene, $C_9$ alkylbenzene, and $C_{10}$ alkylbenzene; (b) separating said transalkylation zone effluent in a fractionation zone to produce a lower boiling fraction comprising benzene and toluene, a principally $C_8$ alkylbenzene central boiling fraction which is withdrawn as a product, and a higher boiling fraction comprising $C_9$ and $C_{10}$ alkylbenzene; (c) passing said lower boiling fraction into a fractionator at an upper locus and said higher boiling fraction into said fractionator at a lower locus and separating the components of said lower boiling fraction and said higher boiling fraction to produce a principally benzene overhead fraction which is withdrawn as a product, at least one sidecut fraction which contains toluene and $C_9$ alkylbenzene and which is withdrawn from said fractionator intermediate the loci of introduction of said overhead fraction and said higher boiling fraction, and a principally $C_{10}$ alkylbenzene bottoms fraction which is withdrawn as a product; and, (d) recycling said sidecut fraction to said transalkylation zone.

In another embodiment, the present invention relates to a combination aromatics extraction and transalkylation process for producing principally benzene and $C_8$ alkylbenzene products comprising the steps of: (a) transalkylating an admixture of toluene and $C_9$ alkylbenzenes in a transalkylation zone at transalkylation conditions to result in transalkylation zone effluent including benzene, toluene, $C_8$ alkylbenzene, $C_9$ alkylbenzene, and $C_{10}$ alkylbenzene; (b) separating a feedstock containing $C_6$–$C_{10}$ alkylbenzenes and non-aromatics of the same boiling range in an aromatic extraction zone at aromatics extraction conditions to obtain a $C_6$–$C_{10}$ alkylbenzene extract stream; (c) admixing said transalkylation zone effluent and said extract stream and separating the admixture in a fractionation zone to produce a lower boiling fraction comprising benzene and toluene, a principally $C_8$ alkylbenzene central boiling fraction which is withdrawn as a product, and a higher boiling fraction comprising $C_9$ and $C_{10}$ alkylbenzene; (d) passing said lower boiling fraction into a fractionator at an upper locus and said higher boiling fraction into said fractionator at a lower locus and separating the components of said lower boiling fraction and said higher boiling fraction to produce a principally benzene overhead fraction which is withdrawn as a product, at least one sidecut fraction which contains toluene and $C_9$ alkylbenzene and which is withdrawn from said fractionator intermediate the loci of introduction of said lower-boiling fraction and said higher boiling fraction, and a principally $C_{10}$ alkylbenzene bottoms fraction which is withdrawn as a product; and, (e) recycling said sidecut fraction to said transalkylation zone.

In a typical prior art process, the effluent of a toluene transalkylation reaction zone containing benzene, toluene, xylene, $C_9$ aromatics, and aromatics heavier than $C_9$ is separated in a fractionation zone into product and recycle streams each of which contains a high purity single carbon number aromatic component. Benzene, xylene, and aromatics heavier than $C_9$ are withdrawn as product streams, while toluene and $C_9$ aromatics are recycled as two separate, purified streams to the transalkylation zone. In the fractionation zone, reaction zone effluent is typically separated to form benzene as the overhead fraction of a first fractionator, toluene as the overhead fraction of a second fractionator, $C_8$ aromatics as the overhead fraction of a third fractionator, $C_9$ aromatics as the overhead fraction and $C_{10}$ aromatics as the bottoms fraction of a fourth fractionator. The bottoms fraction of each column is passed as feed to the next column in the series. Each fractionator is provided with an overhead condensation and reflux system and a bottoms indirect reboiler system known to one skilled in the art. In one embodiment of the processing scheme of the present invention, a first fractionator separates the reaction zone effluent to result in benzene and toluene as a first overhead fraction and $C_8$–$C_{10}$ alkylaromatics as a first bottoms fraction, which is passed into a second fractionator. There, $C_8$ alkylbenzene is withdrawn as an overhead product stream while $C_9$ and $C_{10}$ alkylaromatics are withdrawn as a second bottoms fraction. The first overhead fraction and the second bottoms fraction are passed into a third fractionator, at separate loci of the column, and separated into an overhead product stream containing benzene, a sidecut recycle stream containing $C_7$ and $C_9$ aromatics in admixture, and a bottoms product stream containing $C_{10}$ aromatics. Each fractionator is provided with typical indirect overhead condensation and indirect bottoms reboiler systems known to one skilled in the art. Benefits of the improved fractionation processing scheme include: (1) elimination of a fourth fractionator including an overhead condensation system and a bottoms reboiler system, and (2) reduction of utility requirement as $C_9$ vapors in effect provide direct heat to vaporize benzene for the benzene-toluene split.

BRIEF DESCRIPTION OF THE DRAWING

The attached drawing illustrates, in the form of a flow sheet, the principal steps of a preferred embodiment of the invention.

DESCRIPTION OF THE DRAWING

This invention can be more clearly described and illustrated with reference to the attached drawing in which a preferred embodiment of the invention is depicted. While of necessity certain limitations must be present in such a schematic description, no intention is meant thereby to limit the generally broad scope of the invention. The first step of the present inventive process comprises transalkylating toluene and $C_9$ alkylbenzenes in a transalkylation zone. A reactant stream comprising toluene alone, $C_9$ alkylbenzene alone, or an admixture of toluene and $C_9$ alkylbenzene is introduced into the transalkylation zone 1 via conduit 2. Both toluene and $C_9$ alkylbenzene are commonly available in a satisfactory purity as produced in the fractionation zone of an aromatics extraction process in which either sulfolane or a glycol is utilized to separate aromatic from non-aromatic components. Alternatively, if the fresh feed reactant stream is a mixture of alkylaromatic separated by an extraction process, different feed loci may be employed. For example, but not as a limitation to the present inventive concept, a reactant stream comprising $C_6$ to $C_{10}$ alkylbenzenes is preferably introduced into the present process via conduit 16; a reactant stream comprising $C_6$ to $C_7$ alkylbenzenes is preferably introduced via conduit 17; a reactant stream comprising $C_8$ to $C_{10}$ alkylbenzenes is preferably introduced via conduit 18; a reactant stream comprising $C_9$–$C_{10}$ alkylbenzenes is preferably introduced via conduit 19; etc. In the present illustration, the reactant stream comprises 15.4 moles/hour toluene and 15.5 moles/hour $C_9$ alkylbenzenes. Prior to its introduction into the transalkylation zone, the reactant stream in conduit 2 is admixed with a recycle stream comprising 26.7 moles/hour toluene and 9.3 moles/hour $C_9$ alkylbenzene. The recycle stream is prepared as described hereinbelow and passed via conduit 3, admixed with the reactant stream in conduit 2, and introduced into the transalkylation zone 1 via conduit 2. The transalkylation zone of the present process contains heating, pumping, recycle gas compression, reaction, and separation means, etc., all known in the art. A hydrogen gas stream containing 8.5 moles/hour hydrogen is introduced into the transalkylation zone via conduit 4, and a light gas stream including 7.0 moles/hour $C_1$ to $C_4$ hydrocarbons is withdrawn via conduit 5. The resultant effluent of the transalkylation zone 1 is passed via conduit 6 into a first fractionation column 7, which contains conventional trays, reboiling means, refluxing means, etc., all known in the art. Transalkylation zone effluent introduced into the first fractionator 7 includes 6.5 moles/hour benzene, 26.7 moles/hour toluene, 22.0 moles/hour xylene and ethylbenzene, 9.3 moles/hour $C_9$ alkylbenzene, and 1.5 moles/hour $C_{10}$ alkylbenzene. In the first fractionator, a separation is effected to result in a first overhead fraction including 6.5 moles/hour benzene and 26.7 moles/hour toluene and a first bottoms fraction including 22.0 moles/hour xylene and ethylbenzene, 9.3 moles/hour $C_9$ alkylbenzene, and 1.5 moles/hour $C_{10}$ alkylbenzene. The latter fraction is passed via conduit 8 into a second fractionator 9 which also contains conventional trays, reboiling means, refluxing means, etc., all known in the art. A second overhead fraction including 22.0 moles/hour xylene and ethylbenzene is withdrawn as a product stream via conduit 10, and a second bottoms fraction including 9.3 moles/hour $C_9$ alkylbenzene and 1.5 moles/hour $C_{10}$ alkylbenzene is withdrawn via conduit 11. As illustrated in the attached drawing, the first overhead fraction is withdrawn from the first fractionator and introduced via conduit 12 into a third fractionator 13 at an upper locus, and the second bottoms fraction is introduced via conduit 11 into the third fractionator at a lower locus. The third fractionator contains conventional trays, reboiling means, refluxing means, etc., all known in the art. Benzene is withdrawn at a rate of 6.5 moles/hour as an overhead product fraction via conduit 14, toluene and $C_9$ alkylbenzene are withdrawn in admixture at rates of 26.7 moles/hour and 9.3 moles/hour, respectively, via conduit 3 from a point of the column between the points of introduction of streams 11 and 12, and $C_{10}$ alkylbenzene is withdrawn at 1.5 moles/hour as a bottoms product fraction via conduit 15. The toluene and $C_9$ alkylbenzene stream withdrawn from fractionator 13 via conduit 3 is recycled to the transalkylation zone as described hereinabove. Certain conventional equipment, e.g., pumps, valves, instrumentation, etc., necessary for the operation of the embodiment described in the foregoing have been omitted from the drawing and description thereof. The use and placement of such conventional items will be obvious to those skilled in the art. The foregoing description illustrates some of the advantages of the present invention, but is not intended as limiting the inventive concept to the embodiment presented.

DETAILED DESCRIPTION OF THE INVENTION

Reactants suitable for the present process are toluene alone, $C_9$ alkylbenzene alone, or an admixture of the two. Both toluene and $C_9$ alkylbenzene are commonly prepared as product streams of an aromatics extraction process wherein aromatic components of a feedstock containing $C_6$–$C_9$ alkylbenzenes and non-aromatics of the same boiling range are extracted usually by either sulfolane or a glycol solvent in a solvent phase, the aromatic components are separated by fractionation from the solvent, and the aromatic components are separated in a fractionation zone into benzene, toluene, $C_8$ alkylbenzene, and $C_9$ alkylbenzene cuts. In this way, high purity aromatic streams are made available. Toluene thus prepared normally contains about 5 to 500 ppm. by weight contaminants while the $C_9$ alkylbenzene stream usually contains less than about 1.0 percent by weight contaminant. Suitable $C_9$ alkylbenzene reactants for the present process include 1,2,3 trimethylbenzene, 1,2,4 trimethylbenzene, 1,3,5 trimethylbenzene, 1,2 methylethylbenzene, 1,3 methylethylbenzene, 1,4 methylethylbenzene, n-propylbenzene, and isopropylbenzene. Of these, the trimethylbenzene isomers are preferred. Although toluene alone, or $C_9$ alkylbenzene alone is a suitable fresh feed reactant for the present process, an admixture of the two wherein toluene comprises 75 to 25 molar percent and $C_9$ alkylbenzene comprises 25 to 75 molar percent is preferred.

Benzene and xylene are the desired products of the present process. In regard to the latter, paraxylene is the preferred isomer, although it is not prepared in a purified form by the present invention but is prepared in admixture with other xylene isomers and ethylbenzene. While a transalkylation reaction wherein a methyl or ethyl radical passes from one alkylbenzene ring to another is the principal reaction, dealkylation also takes place with a net result of formation of $C_1$–$C_4$ paraffins and lower yields of $C_{10}$ alkylbenzene than would be predicted by a simple transalkylation reaction.

To effect a transalkylation reaction, the present invention incorporates a transalkylation catalyst, but no limitation is intended in regard to a specific catalyst. One skilled in the art is familiar with several transalkylation catalyst suitable for use in the present invention. For example, in U.S. Pat. No. 3,849,340 a catalytic composite comprising a mordenite component having a $SiO_2/Al_2O_3$ mole ratio of at least 40:1 prepared by acid extracting $Al_2O_3$ from mordenite prepared with an initial $SiO_2/Al_2O_3$ mole ratio of about 12:1 to about 30:1 and a metal component selected from copper, silver and zirconium is described. Friedel-Crafts metal halides such as aluminum chloride have been employed with good results and are suitable for use in the present process. Hydrogen halides, boron halides, Group I-A metal halides, iron group metal halides, etc., have been found suitable. Refractory inorganic oxides, combined with the above mentioned and other known catalytic materials, have been found useful in transalkylation operations. Crystalline aluminosilicates have also been employed in the art as transalkylation catalysts. Other catalysts including a mordenite component and a metal component selected from a Group VIII metal activator are known in the art.

Transalkylation reactions are preferably effected at a temperature of about 400° to 1000° F. in a continuous manner utilizing a catalyst in a fixed bed. A vapor phase operation, preferably in the presence of hydrogen, is more desirable than a liquid phase operation. Contact time, expressed in terms of liquid hourly space velocity, of about 0.1 to about 20 hours$^{-1}$ or more may be utilized. A pressure of about 1 to 60 atmospheres is recommended to effect transalkylation of alkylbenzenes such as toluene and $C_9$ alkylbenzene. The transalkylation step in the present process may be embodied in a batch type reaction scheme or a continuous type reaction scheme, the latter being preferable. This is effected by employing the transalkylation catalyst as a fixed bed in a reaction zone of the transalkylation zone and continuously charging the reactant stream into the reaction zone, passing the hydrocarbons over the catalyst bed, and withdrawing the converted hydrocarbons from the reaction zone. A large variety of vessels suitable for use as a reactor in a transalkylation reaction zone is well known in the art.

After cooling to about 100° F., the resultant effluent of the transalkylation reactor is passed into a separation drum and flashed to form a principally hydrogen gas phase and a liquid phase, the former being recycled to the reaction zone, although a portion may also be withdrawn from the process for the purpose of maintaining hydrogen purity in the hydrogen recycle gas stream at a suitably high value, and the latter phase being passed into a stripping column wherein light gases including $C_1$–$C_4$ paraffins are stripped from the liquid phase. To accomplish the routine cooling, heating, and separation found in the transalkylation zone, oil or gas fired heaters, indirect heat exchange means, a separation drum, a stripping column, a hydrogen recycle gas, compressor, etc., all known in the art are required. The liquid effluent of the transalkylation zone, stripped of light hydrocarbons, contains $C_6$–$C_{10}$ alkylbenzenes, including benzene, unreacted toluene, $C_8$ alkylbenzene, unreacted $C_9$ alkylbenzene, and $C_{10}$ alkylbenzene.

As described hereinabove, toluene and $C_9$ alkylbenzenes suitable as reactants for the present process are commonly prepared as product streams from an aromatics extraction process and its associated fractionation zone. The aromatics extraction process is well known in the art and normally comprises two zones, an extraction zone, usually referred to as the extraction section, and fractionation zone or section. In the extraction section, a hydrocarbon feedstock normally in a boiling range of about 150° to 350° F. and including about 30–60 percent by volume aromatics and 70–40 percent paraffins and naphthenes is introduced into an extractor wherein the feedstock is contacted with a solvent, normally sulfolane or a glycol. Two liquid phases result, the lighter one being a raffinate or principally non-aromatic phase which is withdrawn as a product stream, and a heavier one which is referred to as the rich solvent phase and contains principally aromatic extract and solvent, but also contains non-aromatic hydrocarbon impurities. When sulfolane is the solvent, extraction conditions include a temperature of about 100° to 300° F., a pressure of about 10 to 30 atmospheres, and a solvent/hydrocarbon feed volumetric ratio of about 1.0 to 6.0. The rich solvent phase is further processed to separate solvent, extract, and non-aromatic components by a combination of extractive distillation and steam stripping operations, at extractive distillation and steam stripping conditions selected to result in a lean solvent relatively free of hydrocarbons and suitable for recycling to the extractor, a non-aromatic rich stream suitable for recycling to the extractor, and an extract including at least 99.5 percent $C_6-C_{10}$ alkylbenzene. All extraction and distillation equipment is well known in the art, and various process patents describe the extraction and solvent separation steps fully. The following U.S. patents are useful to the further understanding of the process and equipment incorporated in the art of separating $C_6-C_{10}$ alkylaromatics from non-aromatics of the same boiling range by extraction and extractive distillation: U.S. Pat. Nos. 3,435,087, 3,361,664, 3,433,735, 3,466,345, 3,619,419, 3,207,692, 3,338,823, 3,661,771, 2,094,047, 2,902,413, 3,396,101, etc. The extract product of the extraction section is commonly passed into a fractionation section, wherein ordinary distillation techniques are used to separate the $C_6-C_{10}$ alkylbenzenes into benzene, toluene, $C_8$ alkylbenzene, $C_9$ alkylbenzene, and heavier fractions. Two of these fractions, the toluene fraction and the $C_9$ alkylbenzene fraction are suitable as reactants in the transalkylation zone of the present process. However, a processor who is producing benzene and xylene products by transalkylation of toluene and $C_9$ alkylbenzene is also likely to be preparing BTX products by an aromatics extraction process, and accordingly, it is beneficial to combine the fractionation zones of the aromatics extraction process and the transalkylation process by admixing extract effluent of the aromatics extraction process and the liquid effluent from the transalkylation zone, and passing the admixture into a single fractionation zone. In this case, no fresh reactants need be introduced into the transalkylation zone except those which are introduced into the fractionation zone of the present process in the extract stream from the aromatics extraction zone, separated in the fractionation zone, and recycled to the transalkylation zone as described hereinbelow.

The inlet stream to the fractionation zone of the present process is the liquid effluent stream of the transalkylation zone, alone, or admixed with the extract stream of an aromatics extraction zone as described hereinabove, and contains benzene, toluene, and $C_8-C_{10}$ alkylbenzenes. In conventional practice, said inlet stream to the fractionation zone is treated to reduce olefin content to an acceptable level prior to introduction of the inlet stream into the first fractionator. Treatment is effected by passing the inlet stream at a temperature of about 300° to 500° F. and sufficient pressure to maintain a liquid phase, about 15 to 40 atmospheres, over a suitable natural clay at a liquid hourly space velocity of about 0.4 to 5.0 hour$^{-1}$. In prior art processes, said inlet stream is then commonly introduced into a first fractionator, the bottoms fraction of the first fractionator is introduced into a second fractionator, the bottoms fraction of the second fractionator is introduced into a third fractionator, and the bottoms fraction of the third fractionator is introduced into a fourth fractionator; benzene, toluene, $C_8$ alkylbenzene, and $C_9$ alkylbenzene are withdrawn as condensed overhead product fractions from the first through fourth fractionators, respectively, and $C_{10}$ alkylbenzene is withdrawn as a bottoms product fraction of the fourth fractionator. In one embodiment of the present inventive process, said inlet stream is introduced into a first fractionator from which a benzene-toluene fraction is withdrawn as an overhead stream and a $C_8-C_{10}$ alkylbenzene fraction is withdrawn as a bottoms stream. The $C_8-C_{10}$ alkylbenzene fraction is introduced into a second fractionator, in which a separation is effected to a result in a $C_8$ alkylbenzene overhead fraction and a $C_9-C_{10}$ bottoms fraction. The $C_8$ alkylbenzene overhead fraction is withdrawn and recovered as a product stream. Said benzene-toluene fraction is introduced into a third fractionator at an upper locus and said $C_9-C_{10}$ alkylbenzene fraction is introduced into the third fractionator at a lower locus. From the third fractionator, an overhead benzene fraction is withdrawn as a product stream, a liquid sidecut fraction is withdrawn at a point intermediate the points of introduction of said benzene-toluene fraction and said $C_9-C_{10}$ alkylbenzene fraction, and a $C_{10}$ alkylbenzene bottoms fraction is withdrawn as a product stream. The sidecut fraction contains toluene and $C_9$ alkylbenzene in admixture and is passed as a recycle stream to the transalkylation zone as described hereinabove. In another embodiment of the present invention, said inlet stream to the fractionation zone is introduced into a first fractionator wherein a separation is effected to produce a $C_6-C_8$ overhead fraction and a $C_9-C_{10}$ bottoms fraction. The former fraction is withdrawn and passed into a second fractionator in which a second separation results in a benzene-toluene overhead fraction and a $C_8$ alkylbenzene bottoms fraction, which is withdrawn and recovered as a product stream. As in the first embodiment of the present invention described above, the benzene-toluene fraction is introduced into a third fractionator at an upper locus and the $C_9-C_{10}$ alkylbenzene fraction is introduced into the third fractionator at a lower locus. A third separation is effected, resulting in a benzene overhead fraction, a liquid sidecut fraction containing toluene and $C_9$ alkylbenzene in admixture, and a $C_{10}$ bottoms fraction. The benzene overhead and $C_{10}$ bottom fractions are withdrawn and recovered as product streams while the sidecut fraction is withdrawn and recycled to the transalkylation zone. The fractionation zone of the present process utilizes fractionation trays, condensing means, reboiling means, pumps, valves, instruments, heat exchangers, etc., common in similar processing facilities, and all are known in the art.

The toluene $C_9$ alkylbenzene sidecut fraction is described hereinabove as being withdrawn from the third fractionator at a locus intermediate the loci of introduction into the third fractionator of the benzene-toluene fraction and the $C_9$–$C_{10}$ alkylbenzene fraction. It is also within the scope of the present invention to withdraw the sidecut fraction from a plurality of loci of the third fractionator, all of said loci being intermediate the loci of introduction of the benzene-toluene fraction and the $C_9$–$C_{10}$ alkylbenzene fraction.

While the third fractionator of the present process is described hereinabove as a single vessel, it is also within the scope of this invention to utilize two fractionation vessels. In this case, the benzene-toluene fraction is introduced into the first vessel preferably at an intermediate point, and the $C_9$–$C_{10}$ alkylbenzene fraction is introduced into the second vessel, preferably also at an intermediate point. A reboiling system is provided at the bottom of the second vessel and a condensing and refluxing system is provided at the top of the first vessel. Bottoms liquid of the first vessel is introduced onto the top tray of the second vessel and vapors from the top of the second vessel are introduced without cooling below the bottom tray of the first vessel, thereby simulating a single third fractionation column with the use of two vessels. Benzene is withdrawn as an overhead product stream from the first vessel, and $C_{10}$ alkylbenzene is withdrawn as a bottoms product stream from the second vessel. Toluene and $C_9$ alkylbenzene is withdrawn from the fractionation zone as a liquid stream in a single conduit as a portion of the bottoms stream of the first vessel and recycled to the transalkylation zone.

The benzene product fraction is described hereinabove as being withdrawn as an overhead fraction from the third fractionator, however, it is within the scope of this invention to withdraw the benzene fraction as a sidecut liquid stream at a point above the point of introduction of the benzene-toluene fraction and below the top tray of the third fractionator, preferably at about the fifth tray below the top tray.

Operating pressure in each of the three fractionators is about 1 to 5 atmospheres, with operating temperatures corresponding to the pressure and fluid composition. At one atmosphere pressure, the temperature at the top of the first fractionator is about 225° F., at the top of the second fractionator it is about 275° F., and the top of the third fractionator it is about 175° F. Sufficient heat is introduced into the reboiler of each column to result in a reflux/feed molar ratio of about 1/1 to 4/1, about 1.4/1 to 2/1 being preferred, with only the upper feed to the third fractionator considered in application of the stated molar reflux/feed ratio.

By practice of the present invention a reduction of the number of fractionation vessels from 4 to 3 may be achieved compared to prior art processes, a reduction of capital equipment is achieved as only 3 reboiling and 3 condensing systems are required in the present invention compared with 4 reboiling and 4 condensing systems in a conventional 4 fractional column system, and a substantial reduction in utility usage resulting from a lower vaporization and condensation requirement is obtained. This latter benefit is a result of: (a) effective use of $C_9$ alkylbenzene vapors to provide direct reboiling heat to drive the benzene-toluene separation; (b) withdrawal of the $C_9$ alkylbenzene fraction as a liquid sidecut stream rather than a condensed overhead fraction; and, (c) a substantial reduction of the sum of the inlet streams introduced into the fractionation columns, thereby reducing the total refluxing requirement. In a process in which conventional indirect heating and cooling mediums are utilized in the reboiling and condensing means, respectively, e.g., steam as the heat medium in an indirectly heated reboiler or fuel gas or oil as the heat medium in an indirectly heated furnace reboiler, and cooling water as the condensing and cooling medium of an indirectly cooled overhead vapor condenser, it is expected that use of the present inventive process will result in a utilities saving (heat and cooling medium) of about 5–20 percent compared to prior art processes.

I claim as my invention:

1. A transalkylation process for producing principally benzene and $C_8$ alkylbenzene products comprising the steps of:
   a. transalkylating an admixture of toluene and $C_9$ alkylbenzenes in a transalkylation zone at transalkylation conditions to result in transalkylation zone effluent including benzene, toluene, $C_8$ alkylbenzene, $C_9$ alkylbenzene, and $C_{10}$ alkylbenzene;
   b. separating said transalkylation zone effluent in a fractionation zone to produce a lower boiling fraction comprising benzene and toluene, a principally $C_8$ alkylbenzene central boiling fraction which is withdrawn as a product, and a higher boiling fraction comprising $C_9$ and $C_{10}$ alkylbenzene;
   c. passing said lower boiling fraction into a fractionator at an upper locus and said higher boiling fraction into said fractionator at a lower locus and separating the components of said lower boiling fraction and said higher boiling fraction to produce a principally benzene overhead fraction which is withdrawn as a product, at least one side-cut fraction which contains toluene and $C_9$ alkylbenzene and which is withdrawn from said fractionator intermediate the loci of introduction of said lower boiling fraction and said higher boiling fraction, and a principally $C_{10}$ alkylbenzene bottoms fraction which is withdrawn as a product; and,
   d. recycling said side-cut fraction to said transalkylation zone.

2. A combination aromatics extraction and transalkylation process for producing principally benzene and $C_8$ alkylbenzene products comprising the steps of:
   a. transalkylating an admixture of toluene and $C_9$ alkylbenzene in a transalkylation zone at transalkylation conditions to result in a transalkylation zone effluent including benzene, toluene, $C_8$ alkylbenzene, $C_9$ alkylbenzene, and $C_{10}$ alkylbenzene;
   b. separating a feedstock containing $C_6$–$C_{10}$ alkylbenzenes and non-aromatics of the same boiling range in an aromatics extraction zone at aromatics extraction conditions to obtain a $C_6$–$C_{10}$ alkylbenzene extract stream;
   c. admixing said transalkylation zone effluent and said extract stream and separating the admixture in a fractionation zone to produce a lower boiling fraction comprising benzene and toluene, a principally $C_8$ alkylbenzene central boiling fraction which is withdrawn as a product, and a higher boiling fraction comprising $C_9$ and $C_{10}$ alkylbenzene;
   d. passing said lower boiling fraction into a fractionator at an upper locus and said higher boiling fraction into said fractionator at a lower locus and separating the components of said lower boiling fraction and said higher boiling fraction to produce a principally benzene overhead fraction which is withdrawn as a product, at least one sidecut fraction which contains toluene and $C_9$ alkylbenzene and which is withdrawn from said fractionator intermediate the loci of introduction of said lower-boiling fraction and said higher boiling fraction, and a principally $C_{10}$ alkylbenzene bottoms fraction which is withdrawn as a product; and,
   e. recycling said sidecut fraction to said transalkylation zone.

* * * * *